(12) United States Patent
Fukuda et al.

(10) Patent No.: US 6,323,332 B1
(45) Date of Patent: Nov. 27, 2001

(54) SULFOTRANSFERASE FOR HNK-1 GLYCAN

(75) Inventors: Minoru Fukuda; Edgar Ong, both of San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/235,103

(22) Filed: Jan. 21, 1999

Related U.S. Application Data

(60) Provisional application No. 60/072,005, filed on Jan. 21, 1998.

(51) Int. Cl.$^7$ ............................... C12N 9/00; C12N 9/10; C07H 21/04
(52) U.S. Cl. .................... 536/23.2; 435/183; 536/23.1
(58) Field of Search ................................. 435/183, 193; 530/389.1; 536/23.1, 23.2

(56) References Cited

PUBLICATIONS

Adams et al. GenBank Accession No. AA338789, Apr. 21, 1997.*

Hillier et al. Genbank Accession No. R18331, Apr. 14, 1995.*

Aigner et al., "CD24, a Mucin–Type Glycoprotein, Is a Ligand for P–Selectin on Human Tumor Cells," *Blood*, 89:3385–3395 (1997).

Bakker et al., "Expression Cloning of a cDNA Encoding a Sulfotransferase Involved in the Biosynthesis of the HNK–1 Carbohydrate Epitope," *J. Biol. Chem.*, 272(47):29942–29946 (1997).

Chou et al., "Characterization and Developmental Expression of a Novel Sulfotransferase for the Biosynthesis of Sulfoglucuronyl Glycolipids in the Nervous System," *J. Biol. Chem.*, 268:330–336 (1993).

Fukuta et al., "Molecular Cloning and Expression of Chick Chondrocyte Chondroitin 6–Sulfotransferase," *J. Biol. Chem.*, 270:18575–18580 (1995).

Honke et al., "Molecular Cloning and Expression of cDNA Encoding Human 3'–Phosphoadenylylsulfate:galactosylceramide 3'–Sulfotransferase," *J. Biol. Chem.*, 272:4864–4868 (1997).

Jungalwala, F.B., "Expression and Biological Functions of Sulfoglucuronyl Glycolipids (SGGLs) in the Nervous System—A Review," *Neurochem. Res.*, 19:945–957 (1994).

Jackson et al., "CD24, a Signal–transducing Molecule Expressed on Human B Cells, Is a Major Surface Antigen on Small Cell Lung Carcinomas," *Cancer Res.*, 52:5264–5270 (1992).

Kobayashi et al., "Molecular Cloning and Expression of Chinese Hamster Ovary Cell Heparan–sulfate 2–Sulfotransferase," *J. Biol. Chem.*, 272:13980–13985 (1997).

Mohan et al., "Sulfoglucuronyl Glycolipids Bind Laminin," *J. Neurochem.*, 54:2024–2031 (1990).

Oka et al., "A Novel Glucuronyltransferase in Nervous System Presumably Associated with the Biosynthesis of HNK–1 Carbohydrate Epitope on Glycoproteins," *J. Biol. Chem.*, 267:22711–22714 (1992).

Schachner et al., "Glycans and the modulation of neural-recognition molecule function," *Trends Neurosci.*, 18:183–191 (1995).

Shworak et al., "Molecular Cloning and Expression of Mouse and Human cDNAs Encoding Heparan Sulfate D–Glycosaminyl 3–O–Sulfotransferase," *J. Biol. Chem.*, 272:28008–28019 (1997).

Terayama et al., "Cloning and functional expression of a novel glucuronyltransferase involved in the biosynthesis of the carbohydrate epitope HNK–1," *Proc. Natl. Acad. Sci. USA*, 94:6093–6098 (1997).

\* cited by examiner

Primary Examiner—Rebecca E. Prouty
Assistant Examiner—Manjunath Rao
(74) *Attorney, Agent, or Firm*—Campbell & Flores LLP

(57) ABSTRACT

Sulfotransferases that synthesize the HNK-1 carbohydrate epitope by adding a sulfate group to GlcAβ1→3Galβ1→4GlcNAcβ1→R to form glycan sulfo→3GlcAβ1→3Galβ1→4GlcNAcβ1→R. They are exemplified by human (hu-HNK-1ST) and mouse (mHNK-1ST) sulfotransferases. Also provided are related peptides, antibodies, nucleic acids and methods.

6 Claims, 5 Drawing Sheets

Figure 1

```
ATGCACCATCAGTGGCTCCTGCTGGCTGCAGTGCTTTGGGTGATTTCATGTTC
ATGGTGGCCAGCAAGTTCATCACGTTGACCTTTAAGGATCCGGATGGGTATAG
TGCCAAACAGGAGTTTGTTGTTCCTGACGACCATGCCGGAAGCAGAGAAGCTAA
GAGGAGAGAAGCATTTCCTGAAGTCCCGAAGCCAACTGGGAAGATGCTTTCG
GACAGCCGTCCTGATCAGCCCCGGTTATCTGGAGCGGCTGAGCTCATCAG
AAACACCTGCAAGGAGGAGGCTCTGCGAACCTCTCACACCGAGGTCTGA
AGTTCGTCCTGGATCGAATATTGTCTGTGACAAGCACAAGATTCTTTCTGTCA
GACTCCCAAGGTGGGCAACACCAGTGAAGAAAAGTGCTGATCGTCCTAAATG
GAGCATTTCTTCCATGAAGAGATTCCTGAAATGTAGTCCATGACCATGAGA
AAATGGCCTTCCACGCCTCTCCTTCAGCAAATAGGAATTCAGAAGCGAT
TGAAACATACTTCAAGTTTTATTGTGAGAGATCCCTTTGAAAGACTGATTTC
TGCCCTTTAAGGATAAGTTTGTCACAATCCTGATTCGAGCCTTGGTACAGGCA
TGAGATAGCCCCAGGCATTATTAGAAAGTACCGGAAGAACCGGACAGAGACCC
GGGGGATCCAGTTTGAAGATTTTGTGCGCTACCTGGGTGATCCAAACCGCAGG
TGGTTAGACCTTCAGTTGGGACCATATCATCCACTGGGTGACCTACGTTGAA
CTCTGTGCGCCCTGTGAGATCAAGTACAGTGGTGCGGACACCATGAGACCCT
GGAGGCAGATGCCCCTACCATCCTCCGGGCATCAACGAGACATCTGCACCATCTGGTGT
CATACCCCACCATCCCTCCGGGCATCAGCAAACGAGACATCTGCTATGCACAAGGTAGAG
CAGTATTCCTGGGCATCTTTGGGTATCAGAAACCAGATTTCTGCACATTGA
AGGAGACTTTAAGCTCTTTGGGTATCAGAAACCAGATTTCTGCTAAATTAA
```

```
MHHQWLLLAA CFWVIFMFMV ASKFITLTFK DPDGYSAKQE

FVFLTTMPEA EKLRGEKHFP EVPKPTGKML SDSRPDQPPV

YLERLELIRN TCKEEALRNL SHTEVSKFVL DRIFVCDKHK

ILFCQTPKVG NTQWKKVLIV LNGAFSSIEE IPENVVHDHE

KNGLPRLSSF SKIGIQKRLK TYFKFF<u>IVRD PFERL</u>ISAFK

DKFVHNPRFE PWYRHEIAPG IIRKYRKNRT ETRGIQFEDF

VRYLGDPNRR WLDLQFGDHI IHWVTYVELC APCEIKYSVV

GHHETLEADA PYILKEAGID HLVSYPTIPP GITMYNRTKV

EQYFLGISKR DIWHLYAHFE GDFKLFGYQK PDFLLN
```

```
  1' MHHQWLLLAACFWVIFMFMVASKFITLTFKDPDGYSAKQEFVFLTAMPEAEKLRGEKHFS
     ************************************.***.***..**..***..
  1  MHHQWLLLAACFWVIFMFMVASKFITLTFKDPDVYSAKQEFLFLTTMPEVRKLPEEKHIP

61' EVMKPTGKMLSESHPDQPPVYLERLELIRNACKEEALRNLSHTEVSKFVLDRIFVCDKHK
     *..*****..**:..*:***:*****:******....*:.:***.**********
 61  EELKPTGKELPDSQLVQPLVYMERLELIRNVCRDDALKNLSHTPVSKFVLDRIFVCDKHK

121' ILFCQTPKVGNTQWKKVLIVLNGAFSSIEEIPENVVHDHEKNGLPRLSSFSKIGIQKRLK
     ***********************************************..*..******
121  ILFCQTPKVGNTQWKKVLIVLNGAFSSIEEIPENVVHDHEKNGLPRLSSFSDAEIQKRLK

181' TYFKFFIVRDPFERLISAFKDKFVHNPRFEPWYRHEIAPGIIRKYRKNRTETRGIQFEDF
     ***********************************************.******
181  TYFKFFIVRDPFERLISAFKDKFVHNPRFEPWYRHEIAPGIIRKYRRNRTETRGIQFEDF

241' VRYLGDPNRRWLDLQFGDHIIHWTYVKLCAPCEIKYSVIGHHETLEADAPYILKEAGID
     ***********************.****.********.**..*********
241  VRYLGDPNHRWLDLQFGDHIIHWTYVELCAPCEIMYSVIGHHETLEDDAPYILKEAGID

301' HLVSYPTIPPGITMYNRTKVEQYFLGISKRDIRRLYARFEGDFKLFGYQKPDFLLN
     *****************.****..**************************
301  HLVSYPTIPPGITVYNRTKVEHYFLGISKRDIRRLYARFEGDFKLFGYQKPDFLLN
```

Figure 4

SULFOTRANSFERASE FOR HNK-1 GLYCAN

This application claims the benefit of U.S. Provisional Application No. 60/072,005, filed Jan. 21, 1998, which is incorporated herein by reference.

This invention was made with government support under grant numbers PO1 CA71932 and RO1 CA33895 awarded by the National Cancer Institute. The government has certain rights in the invention.

BACKGROUND OF THE INVENTION

1. Field of the Invention

The present invention relates to enzymes and more specifically to sulfotransferases that synthesize the HNK-1 carbohydrate epitope.

2. Background Information

Neural and immune cells express certain characteristic carbohydrate glycans on their cell surfaces (Jessell et al. (1985) Ann. Rev. Neurosci. 13, 227–255; Schachner and Martini (1995) Trends Neurosci. 18, 183–191; all references cited herein are incorporated by reference). One such glycan is the HNK-1 carbohydrate epitope, originally discovered by a monoclonal antibody raised against Human Natural Killer cells (Abo and Balch (1981) J. Immunol. 127, 1024–1029). The functional significance of the HNK-1 carbohydrate was first recognized as an autoantigen involved in peripheral demyelinative neuropathy. The structural analysis of glycolipids reacting with these autoantibodies led to the discovery that the HNK-1 epitope is sulfo→3GlcAβ1→3Galβ1→4GlcNAcβ1→R (Chou et al., (1986) J. Biol. Chem. 261, 11717–11725; Ariga et al., (1987) J. Biol. Chem. 262, 848–853).

By using HNK-1-specific antibodies and carbohydrate structural studies, the HNK-1 glycan has been found in a number of neural cell adhesion molecules including N-CAM, myelin-associated glycoprotein, L1, contactin and P0 (Schachner and Martini (1995) Trends Neurosci. 18, 183–191; McGarry et al., (1983) Nature (London) 306, 376–378; Kruse et al., (1984) Nature (London) 311, 153–155; Gennarini et al., (1989) J. Neurosci. Res. 22, 1–12; Voshol et al., (1996) J. Biol. Chem. 271, 22957–22960). The studies, using either monoclonal antibodies or isolated carbohydrates, demonstrated that the HNK-1 glycan is involved in cell-cell and cell-substratum interactions (Keilhauer et al. (1985) Nature (London) 316, 728–730; Mohan et al., (1990) J. Neurochem. 54, 2024–2031).

Expression of the HNK-1 epitope is spatially and developmentally regulated, and is found on migrating neural crest cells, cerebellum and myelinating Schwann cells in motor neurons, but not on those in the sensory neurons (Bronner-Fraser (1986) Dev. Biol. 115, 44–55; Eisenman and Hawkes, (1993) J. Comp. Neurol. 335, 586–605; Martini et al., (1992) Eur. J. Neurosci. 4, 628–639). In addition, the HNK-1 carbohydrate binds to P-selectin and L-selectin (Needham and Schnaar, (1993) Proc. Natl. Acad. Sci., U.S.A. 90, 1359–1363), suggesting that interactions between immune cells and the nervous system may be mediated through binding of the HNK-1 glycan in neural cells.

The HNK-1 glycan is synthesized in a stepwise manner by adding a β1,3-linked glucuronic acid to a precursor N-acetyllactosamine, followed by adding a sulfate group to GlcAβ1→3Galβ1→4GlcNAcβ1→R (Jungalwala, (1994) Neurochem. Res. 19, 945–957; Chou and Jungalwala, (1993) J. Biol. Chem. 268, 330–336). A β-1,3-glucuronyl transferase GlcAT-P (glycoprotein-specific glucuronyltransferase)—which forms an HNK-1 precursor carbohydrate, GlcAβ1→3Galβ1→4GlcNAcβ1→R, in glycoproteins—has been cloned (Terayama et al., (1997) Proc. Natl. Acad. Sci. U.S.A. 94, 6093–6098).

Desulfation experiments have shown that the sulfate group plays a critical role (Mohan et al., (1990) J. Neurochem. 54, 2024–2031). A sulfotransferase involved in the synthesis of HNK-1 has been cloned from rat cells ("raHNK-1ST") (Bakker et al., (1997) J. Biol. Chem. 272, 29942–29946.), although it is believed that the sequence of this sulfotransferase was not publicly known or available until after the date of conception or reduction to practice of the present invention. For the sake of comparison, however, the rat sequence is described herein.

Thus, HNK-1 sulfotransferases have not yet been described as of the present invention. Thus, a need exists for a HNK-1 sulfotransferase involved in synthesizing the HNK-1 glycan. The present invention satisfies this need and provides related advantages as well.

SUMMARY OF THE INVENTION

The present invention provides an HNK-1 sulfotransferase that synthesizes the HNK-1 carbohydrate epitope in cells of the nervous system. The sequences for human and mouse HNK-1 sulfotransferases are provided. The invention also provides peptide portions of HNK-1ST that catalytically active. Also provided are antibodies that bind to human HNK-1ST, as well as cells producing such antibodies.

The present invention also provides a nucleic acid encoding a HNK-1ST polypeptide. In addition, the invention provides polynucleotide sequences that hybridize under stringent conditions to a nucleic acid molecule encoding human HNK-1ST, but not to a nucleic acid molecule encoding rat HNK-1ST. Also provided are vectors containing a nucleic acid molecule of the invention.

The invention further provides methods of synthesizing an HNK-1 carbohydrate epitope on a glycoprotein or glycolipid precursor, by contacting the precursor with human HNK-1ST. Such contacting can occur in vitro or in vivo and, when performed in vitro, can be performed in a cell-free system using a substantially purified precursor or using cells, which express the precursor, in culture. The invention also provides a method of functional expression cloning.

BRIEF DESCRIPTION OF THE DRAWINGS

FIG. 1 shows the nucleotide sequence (SEQ ID NO:1) and translated amino acid sequence (SEQ ID NO:2) of huHNK-1ST (GENBANK/EMBL; accession number AF033827). The start and the end of the open reading frame (ORF) is indicated by brackets. The signal/membrane-anchoring domain is denoted by a dotted line. A sequence homologous to that found in other Golgi-associated sulfotransferases is doubly underlined and the polyadenylation consensus sequences are singly underlined. Potential N-glycosylation sites are marked with asterisks. EcoRI site used for construction of a shorter cDNA HNK-1ST (short) is indicated by an arrow.

FIG. 2 shows the nucleotide sequence (SEQ ID NO:12) of mouse HNK-1 sulfotransferase mHNK-1ST. A sequence homologous to that found in other Golgi-associated sulfotransferases is underlined.

FIG. 3 shows the translated amino acid sequence (SEQ ID NO:13) of mouse HNK-1 sulfotransferase mHNK-1ST. A sequence homologous to that found in other Golgi-associated sulfotransferases is underlined.

FIG. 4 shows a comparison of the amino acid sequences of human HNK-1ST (lower sequence; SEQ ID NO:2) and rat HNK-1ST (upper sequence; SEQ ID NO:4). Identical residues are shown by asterisks and conserved residues are shown by a dot. Numbering of the amino acid residues is shown at the left.

DETAILED DESCRIPTION OF THE INVENTION

Figure 5:
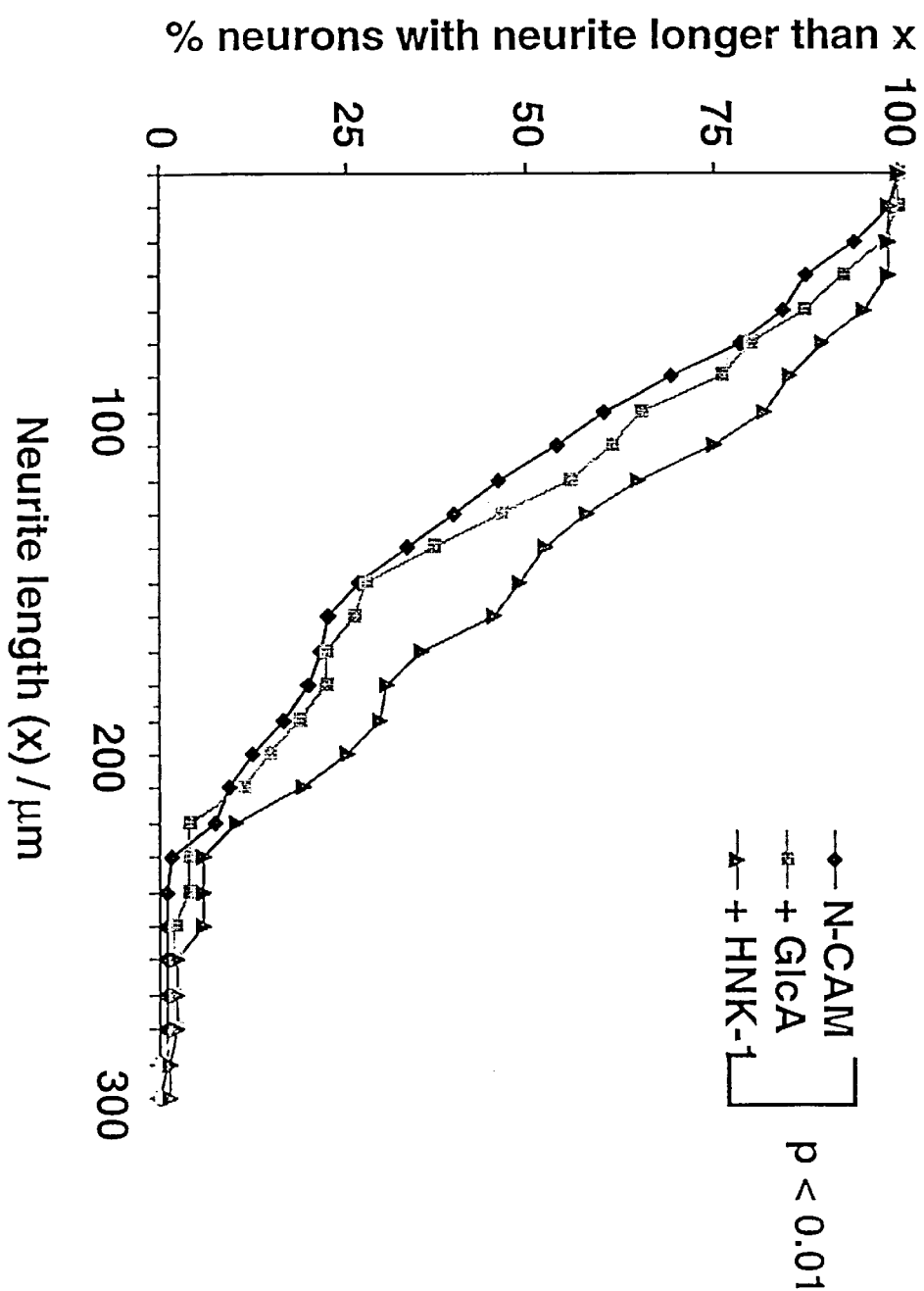
FIG. 5 shows the effect of HNK-1 expression on neural outgrowth. Diagrammatic representation of neurite outgrowth over monolayers of HeLa cells expressing N-CAM, alone (diamonds); HeLa cells expressing N-CAM and glucuronic acid (squares); or HeLa cells expressing N-CAM and HNK-1 (triangles). The diagram shows percentages of neurons (ordinate) with particular neurite length exceeding the values given in the abscissa. The mean neurite lengths over the different monolayers were compared using a Student t-test (p<0.01).

The present invention provides substantially purified HNK-1 sulfotransferase (HNK-1ST) that catalyzes the addition of a sulfate group to GlcAβ1→3Galβ1→4GlcNAcβ1→R to form glycan sulfo→3GlcAβ1→3Galβ1→4GlcNAcβ1→R. The HNK-1 carbohydrate is expressed on various adhesion molecules in cells of the immune system and the nervous system and are suggested to play a role in cell-cell and cell-substratum interactions.

As used herein, the term "HNK-1 sulfotransferase" means any enzyme that catalyzes the addition of a sulfate group to GlcAβ1→3Galβ1→4GlcNAcβ1→R to form glycan sulfo→3GlcAβ1→3Galβ1→4GlcNAcβ1→R. In particular, mammalian sulfotransferases are provided, which are represented by human and mouse sulfotransferases, whose sequences are provided as SEQ ID NO:2 and SEQ ID NO:13, which share a high degree of homology. Excluded from the definition is rat sulfotransferase.

As used herein, the term "substantially purified," when used in reference to a sulfotransferase, means the sulfotransferase is relatively free of contaminating lipids, proteins, nucleic acid molecules or other cellular material associated with a sulfotransferase in a cell, tissue or organ. A substantially purified sulfotransferase can be obtained by using well known purification methods such as affinity chromatography or by expression using a nucleic acid molecule encoding the sulfotransferase. The term "substantially purified" also can refer to a nucleic acid molecule.

Figure 1:
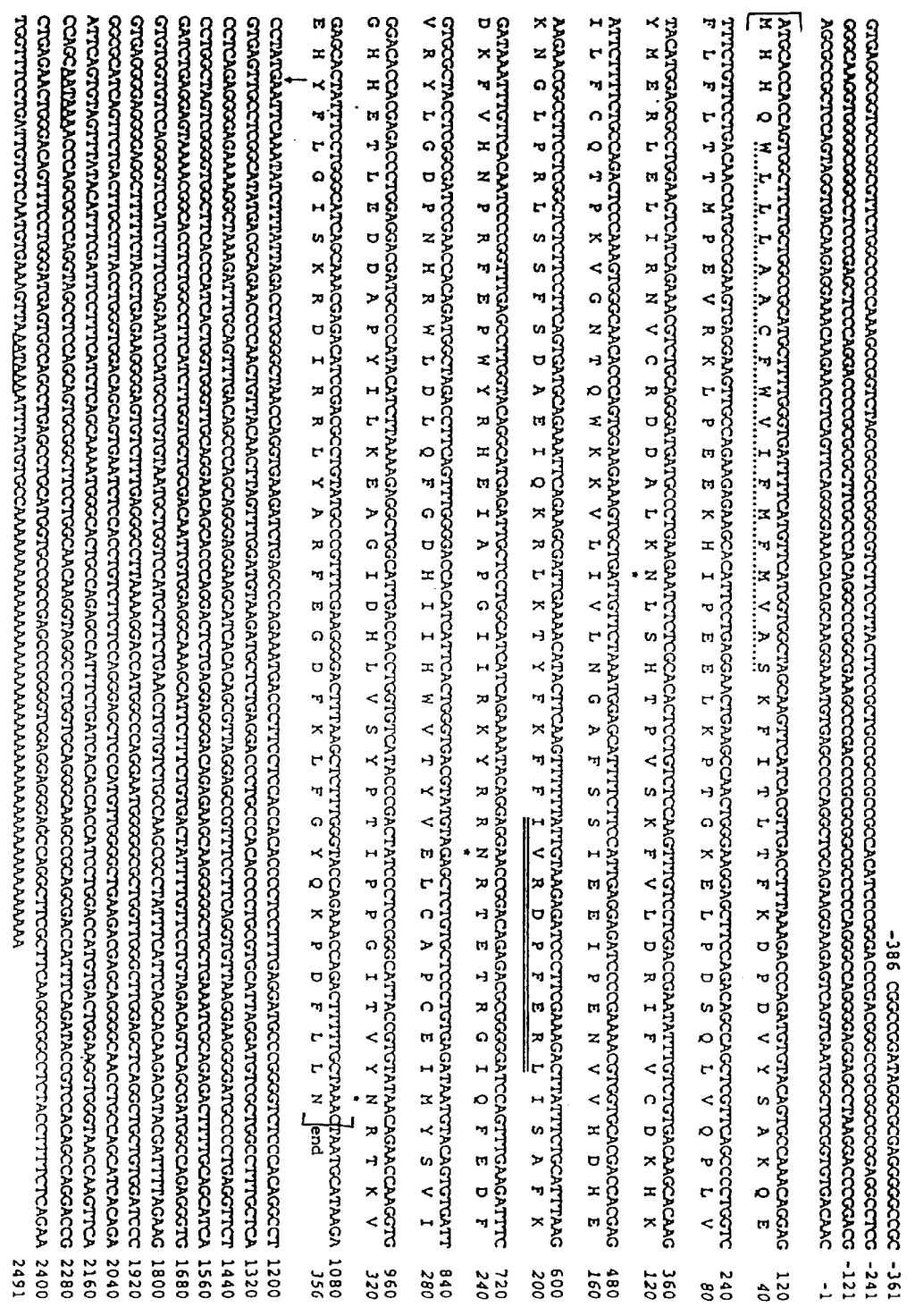

As to the human sequence "huHNK-1ST" the cDNA encoding huHNK-1 sulfotransferase was isolated by functional expression cloning. As shown in FIG. 1, huHNK-1ST has amino acid SEQ ID No:2, encoded by open reading frame (ORF) SEQ ID NO:3. The complete nucleic acid sequence is provided as SEQ ID NO:1.

A mutant Chinese hamster ovary cell line, Lec2, which stably expresses the human neural cell adhesion molecule (N-CAM) was established as described below (Lec2-NCAM). Lec2-NCAM was co-transfected with a human fetal brain cDNA library, a cDNA encoding the rat glucuronyltransferase that forms a precursor of the HNK-1 carbohydrate and a vector encoding the polyoma large T antigen. Transfected Lec2-NCAM cells expressing the HNK-1 glycan were enriched by fluorescence activated cell sorting. Sibling selection of recovered plasmids resulted in the isolation of a cDNA encoding human HNK-1 sulfotransferase.

The deduced amino acid sequence of huHNK-1ST (SEQ ID NO: 2) indicates that the enzyme is a type II membrane protein. Sequence analysis revealed the presence of a short amino acid sequence in the presumed catalytic domain that is highly homologous to the corresponding sequence in previously cloned golgi-associated sulfotransferases. In addition, huHNK-1ST shares about 90% sequence identity with rat HNK-1ST or "raHNK-1ST" (SEQ ID NO:4; upper sequence of FIG. 4; see also Bakker et al., (1997) J. Biol. Chem. 272, 29942–29946).

The invention also provides peptide portions of HNK-1ST that catalytically active. Amino acid sequences are presented for the following enzymes: human HNK-1ST (huHNK-1ST), mouse HNK-1ST (muHNK-1st), rat HNK-1ST (raHNK-1ST), hamster heparin sulfate 2-O-sulfotransferase (haHep2ST), chick chondroitin sulfate 6-O-sulfotransferase (chCho6ST), human galactosylceramide sulfotransferase (huGalCer-ST) and human heparan sulfate 3-O-sulfotransferase (hu3-OST)(Fukuta et al., (1995) J. Biol. Chem. 270, 18575–18580; Honke et al., (1997) J. Biol. Chem. 272, 4864–4868; Kobayashi et al., (1997) J. Biol. Chem. 272, 13980–13985; Shworak et al., (1997) J. Biol. Chem. 272, 28008–28019; Bakker et al., (1997) J. Biol. Chem. 272, 29942–29946).

```
huHNK-1ST    187-IVRDPFERL-195    (SEQ ID NO:14)
mHNK-1ST     187-IVRDPFERL-195    (SEQ ID NO:14)
raHNK-1ST    187-IVRDPFERL-195    (SEQ ID NO:14)
haHep2ST     162-VIRDPIERL-170    (SEQ ID NO:5)
chCho6ST     279-LVRDPRAVL-287    (SEQ ID NO:6)
huGalCerST   162-VLRDPARLF-170    (SEQ ID NO:7)
hu2-OST      145-ILRDPSERV-153    (SEQ ID NO:8)
hu2-OST      220-LIRDPFPEI-228    (SEQ ID NO:9)
consensus    XXRDPZZZX
```

In the consensus sequence, x denotes a hydrophobic amino acid and z denotes any amino acid. The number of amino acid residues is shown in both ends. Accordingly, the present invention provides the consensus as active fragment IVRDPFERL (SEQ ID NO:14).

The amount of huHNK-1ST transcript is high in fetal brain compared to fetal lung, kidney and liver, by northern blot of huHNK-1ST and GlcAT-P in various tissues. The blots were hybridized with $^{32}$P-labeled huHNK-1ST cDNA, then with the GlcAT-P cDNA. The expression profile of the huHNK-1ST transcripts was compared to that of GlcAT-P transcripts for various fetal and adult tissues. Expression of huHNK-1ST resulted in the formation of the huHNK-1 epitope on N-CAM and a soluble chimeric form of huHNK-1ST added a sulfate group to a precursor, GlcAβ1→3Galβ1→4GlcNAcβ1→R, to form sulfo→3GlcAβ1→3Galβ1→4GlcNAcβ1→R (see Example II). huHNK-1ST activity was demonstrated in vivo and in vitro using N-CAM, synthetic oligosaccharides and glycolipids as acceptors. These results demonstrate that the cloned huHNK-1ST directs the synthesis of the HNK-1 carbohydrate epitope both on glycoproteins and on glycolipids in the nervous tissues.

A cDNA clone encoding a human sulfotransferase, huHNK-1ST was isolated by expression cloning. Lec2 cells were stably transfected to express human N-CAM, then, those Lec2 cells expressing N-CAM were transiently co-transfected with a human fetal brain cDNA library in pcDNAI, pcDNA3-GlcAT-P and pPSVE1-PyE. pcDNAI has the supF gene while both pcDNA3-GlcAT-P and pPSVE1-

PyE contain only ampicillin resistant gene. Only plasmids derived from pcDNAI can be rescued and amplified in bacteria containing P3 episome such as MC1061/P3 cells in the presence of ampicillin and tetracycline (Seed and Aruffo (1987) Proc. Natl. Acad. Sci., USA 84, 3365–3369). If desired, the N-CAM cDNA also can be co-transfected transiently, since its vector contains only an ampicillin resistant marker. This expression cloning procedure represents an improved method over a previous expression cloning strategy, where a vector encoding polyoma large T antigen was stably expressed (Bierhuizen and Fukuda, (1992) Proc. Natl. Acad. Sci., U.S.A. 89, 9326–9330; Fukuda et al., (1996) Glycobiology 6, 683–689). By avoiding the preparation of stable transfectants, which are necessary for the expression of the acceptor carbohydrates and polyoma large T antigen, the time necessary for cloning has been shortened dramatically. The cloning of the huHNK-1ST cDNA took approximately two and a half months.

The sequence of rat HNK-1ST (raHNK-1st) was recently published (Bakker et al., (1997) J. Biol. Chem. 272, 29942–29946). The method for cloning the raHNK-1ST differs slightly from that disclosed herein because CHOP2 cells, which are Lec2 cells stably expressing the polyoma large T antigen (Cummings et al., (1993) Biochem. Biophys. Res. Commun. 195, 814–822), were used as recipient cells and the N-CAM cDNA was not co-transfected. Lec2 cells stably expressing N-CAM were used as recipient cells herein in order to clone a cDNA that adds the HNK-1 glycan on neural cell adhesion molecules. The amino acid sequence of the disclosed huHNK-1ST is 90.2% identical to the raHNK-1ST (see FIG. 4).

A consensus sequence is present in various Golgi-associated sulfotransferases above. This conserved amino acid sequence can be involved in the binding of PAPS or in catalysis. Notably, this sequence is not shared by N-deacetylase/N-sulfotransferase, which has dual functions and is involved in heparan sulfate synthesis (Hashimoto et al., (1992) J. Biol. Chem. 267, 15744–15750; Eriksson et al., (1994) J. Biol. Chem. 269, 10438–10443). Thus, the N-deacetylase/N-sulfotransferase may have a different evolutionary origin from the other sulfotransferases. Moreover, the consensus sequence discussed above is different from the presumed PAPS binding sequences found among different soluble cytosolic sulfotransferases (Weinshilboum et al., (1997) FASEB J. 11, 3–14). The consensus sequence present in the different Golgi-associated sulfotransferases can be involved in the enzymatic function of the enzymes.

The cloned huHNK-1ST adds the HNK-1 carbohydrate epitope onto N-CAM. Rat GlcAT-P and the raHNK-1ST, in comparison, add the β-glucuronic acid and sulfate into a wide variety of glycoproteins in CHOP2 cells, although none was identified (Bakker et al., (1997) J. Biol. Chem. 272, 29942–29946). These results strongly suggest that GlcAT-P can add glucuronic acid to N-acetyllactosamine present in a wide variety of glycoproteins and huHNK-1ST can use those carbohydrates as acceptor molecules.

The huHNK-1ST transcript is more widely distributed in different human tissues compared to that of GlcAT-P. Both the huHNK-1ST and GlcAT-P transcripts are highly expressed in the brain, suggesting that the cloned huHNK-1ST and GlcAT-P are responsible for the formation of the HNK-1 glycan in the nervous tissues. There are two glucuronyltransferases specific for forming the HNK-1 precursor structure in glycoproteins and glycolipids, respectively (Oka et al., (1992) J. Biol. Chem. 267, 22711–22714). In contrast, the cloned huHNK-1ST adds a sulfate group to both glycoproteins and glycolipids. The huHNK-1ST present in tissues other than the brain also may act on glycolipid acceptors. Alternatively, another GlcAT-P may be acting on glycoprotein acceptors, which may differ in tissue distribution than the one that has been cloned (Terayama et al., (1997) Proc. Natl. Acad. Sci. U.S.A. 94, 6093–6098).

The present invention also provides a mouse sulfotransferase with the amino acid sequence SEQ ID NO:13, encoded by the nucleic acid sequence SEQ ID NO:12. The murine sequences were obtained by methods similar to those used to obtain the human sequence.

The sulfotransferases of the invention can be used to raise antibodies that bind specifically to sulfotransferases such huHNK-1ST and mHNK-1ST and their peptides. It is recognized that a peptide portion of a sulfotransferase may not be immunogenic by itself. However, it is well known that such a hapten can be attached to a carrier molecule so as to be rendered immunogenic (see, for example, Harlow and Lane, *Antibodies: A Laboratory Manual* (Cold Spring Harbor Laboratory Press 1988), which is incorporated herein by reference). Thus, the invention further provides an antibody that specifically binds to HNK-1 sulfotransferase. In addition, the antibody can specifically binds to huHNK-1ST or to mHNK-1ST, but not to HNK-1 sulfotransferase of another species such as rat.

As used herein, the term "antibody" includes an antigen binding fragment of an antibody such as Fv, Fab or F(ab')$_2$. An antibody of the invention also can be, for example, a chimeric antibody, which can be a mouse/human chimera such as a humanized mouse monoclonal antibody, or a bifunctional or heterofunctional antibody, which can contain antigen binding sites from at least two different antibodies, or can be a CDR grafted antibody.

As used herein, the term "epitope" means a structure of a sulfotransferase that binds to a complementary site of an antibody. An epitope can be a series of sequential amino acid residues in a continuous peptide linkage or can be amino acid residues that, while noncontiguous in a sulfotransferase, are in spatial proximity as a consequence, for example, of a secondary or tertiary structure of a sulfotransferase, such that the residues are recognized and specifically bound by an antibody of the invention.

As used herein, the term "specifically binds," when used in reference to an antibody of the invention, means the antibody has a higher affinity to a sulfotransferase as compared to its affinity to other proteins. The affinity of an antibody of the invention generally is at least about $10^5$ mol$^{-1}$. An antibody of the invention having an affinity of at least about $10^7$ mol$^{-1}$ can be particularly useful, for example, to purify a sulfotransferase from a sample containing such a sulfotransferase. For example, an antibody of the invention can be attached to a solid support such as a gel chromatography matrix for affinity purification of a sulfotransferase or peptide portion thereof. Methods for attaching an antibody to a solid support matrix and purifying an antigen by affinity chromatography are well known in the art (see, for example, Hermanson, *Bioconjugate Techniques* (Academic Press 1996); Harlow and Lane, supra, 1988.).

An antibody of the invention can be produced and characterized as disclosed herein or using methods well known in the art (see Harlow and Lane, supra, 1988). Antibodies, including antigen binding fragments of an antibody, also can be produced by chemical synthesis or using recombinant methods (see Sambrook et al., *Molecular Cloning: A laboratory manual* (Cold Spring Harbor Laboratory Press 1989), which is incorporated herein by reference). Chimeric, humanized, CDR grafted and bifunctional antibodies also can be produced using methods well known to those skilled in the art (see, for example, Harlow and Lane, supra, 1988; Hilyard et al., in *Protein Engineering: A practical approach* (IRL Press 1992); see, also, U.S. Pat. Nos. 5,565,332 and 5,403,484, each of which is incorporated herein by reference).

An antibody of the invention can be particularly useful if it is detectably labeled. An antibody of the invention can be detectably labeled by attaching any of a variety of moieties, including, for example, biotin, an enzyme such as alkaline phosphatase, or a fluorochrome. A moiety can be a gamma ray emitting radionuclide such as indium-111 or technetium-99, enabling detection of an antibody using a solid scintillation detector. A detectable label also can be a positron emitting radionuclide such as carbon-11 or a paramagnetic spin label such as carbon-13, which allows detection of an antibody using positron emission transaxial tomography or magnetic resonance imaging, respectively. Methods for selecting and attaching a particular moiety to an antibody are known in the art (see, for example, Hermanson, supra, 1996).

If desired, an antibody of the invention can be a monoclonal antibody, which is produced by a hybridoma cell line. Monoclonal antibodies are well known in the art and can be produced by using routine methods (see, for example, Harlow and Lane, supra, 1988). Monoclonal antibodies produced from a hybridoma cell line are useful, for example, for identifying sites or levels of sulfotransferase expression in a tissue using immunohistochemical techniques.

The present invention also provides a substantially purified nucleic acid encoding a HNK-1 sulfotransferase that catalyzes the addition of a sulfate group to GlcAβ1→3Galβ1→4GlcNAcβ1→R to form glycan sulfo→3GlcAβ1→3Galβ1→4GlcNAcβ1→R. For example, the nucleic acid can have human SEQ NO:1 or encode human amino acid SEQ NO:2, such as human open reading frame SEQ NO:3. In addition, the nucleic acid can have mouse SEQ NO:12 or encode mouse amino acid SEQ NO:13.

A substantially purified nucleic acid molecule of the invention is useful for expressing a sulfotransferase or a sulfotransferase protein. As used herein, the term "substantially purified" means a nucleic acid molecule is relatively free from contaminating materials such as lipids, proteins, carbohydrates or other cellular material normally associated with a nucleic acid in a cell, tissue or organ. For example, a nucleic acid molecule that is chemically synthesized or is produced using recombinant DNA methods is considered substantially purified. Recombinant DNA methods for obtaining a substantially purified nucleic acid molecule are well known in the art and include cloning a sequence or polymerase chain reaction (PCR) amplification of a sequence (see Sambrook et al., supra, 1989; see, also, Erlich, *PCR Technology: Principles and applications for DNA amplification* (Stockton Press 1989), which is incorporated herein by reference).

The invention also provides a vector comprising a nucleic acid molecule encoding a sulfotransferase. As used herein, the term "vector" means a virus or plasmid used to introduce a nucleic acid molecule into a cell or to generate a recombinant nucleic acid molecule and are well known in the art and commercially available. Vectors include, for example, cloning vectors and expression vectors (see, for example, Goeddel, supra, 1990).

A vector comprising a nucleic acid molecule encoding a sulfotransferase can further comprise a regulatory element involved in the regulation of gene expression or of translation of a transcript. Such regulatory elements, including such as promoters, enhancers, silencers, polyadenylation signal sequences, ribosome entry sites, signal peptide encoding sequences, nuclear localization signal encoding sequences and the like are well known in the art and can be inserted into a vector, as desired, using well known methods of recombinant DNA technology (see, for example, Kriegler, *Gene Transfer and Expression: A laboratory manual* (W. H. Freeman and Co. 1990), which is incorporated herein by reference).

Various types of regulatory elements are available and are selected based on the particular purpose for which a vector is being constructed. A promoter element, for example, can be constitutive such as the cytomegalovirus promoter or Rous sarcoma virus promoter or can be inducible such as the metallothionein promoter. In addition, a promoter can be a tissue specific promoter such as the myoD promoter, which is expressed only in muscle cells, or the lck promoter, which is expressed in T cells, or can be a promoter that is active only during a particular stage of development. Similarly, enhancers can be constitutively active and, in addition, can be inducible, resulting in a higher level of expression. Such gene regulatory elements and translation regulatory elements are relatively small and can be synthesized using routine methods of DNA synthesis or can be purchased from commercial sources.

An expression vector can be particularly useful for expressing a sulfotransferase, which can be purified and used as an immunogen to raise anti-sulfotransferase antibodies. A baculovirus vector is particularly useful for this purpose because it can be used to express a large amount of an ISEM. Expression vectors also can be useful for expressing an antisense nucleic acid, which is complementary to a nucleic acid molecule encoding an integrin subunit, or a ribozyme, which can cleave RNA in a sequence specific manner.

The invention further provides a host cell containing the vector. As used herein, the term "host cell" means a unicellular organism or a cell of a multicellular organism that can harbor the vector and allow expression of a polypeptide encoded by the vector. Host cells are known in the art and can be selected based on the particular vector used, required degree of post-translational processing, desired level of expression, and stability of the expressed polypeptide in the host cell. Methods for purifying proteins expressed on a cell surface are well known in the art (see, for example, Thomas et al., *Meth. Enzymol.* 182:499–520 (Academic Press 1990); Pidgeon et al., *Anal. Biochem.* 194:163–173 (1991), each of which is incorporated herein by reference).

A nucleic acid molecule of the invention can be detectably labeled and used as a probe or a PCR primer, which can be labeled or unlabeled, as desired. Various moieties are useful as detectable labels, including, for example, radioactive, fluorescent, luminescent, magnetic, paramagnetic or enzymatic labels. Methods for detectably labeling a nucleic acid molecule are well known in the art (see, for example, Sambrook et al., supra, 1989; see, also, Ausubel et al., *Current Protocols in Molecular Biology* (Green 1995), which is incorporated herein by reference).

The invention provides a nucleic acid molecule that is complementary to a nucleic acid encoding an HNK-1 sulfotransferase. The invention also provides nucleic acids that hybridizes under relatively stringent conditions to a nucleic acid encoding a sulfotransferase. As used herein, the term "relatively stringent hybridization conditions" means conditions that allow hybridization to a nucleic acid molecule encoding a sulfotransferase, but not to a nucleic acid molecule encoding another sulfotransferase. Such conditions can be empirically determined for a nucleic acid molecule that hybridizes to a second nucleic acid molecule encoding a peptide portion of a sulfotransferase, or can be estimated based, for example, on the relative GC:AT content of the hybridizing nucleic acid molecule and the target sequence, length of the hybridizing nucleic acid molecule and number, if any, of mismatches between the hybridizing nucleic acid molecule and the target sequence (see, for example, Sambrook, supra, 1989). An example of a relatively stringent hybridization condition is 0.1×SSPE, 0.1% SDS at 50° C.

Depending on intended use, a nucleic acid molecule used in a hybridization procedure should be at least about ten nucleotides in length, for example, when used as a primer for PCR, or at least about 14 to 16 nucleotides in length, for example, when used as a probe in a hybridization assay such as a Southern blot, northern blot or other similar "blot" analysis (see, for example, Innis et al., *PCR Protocols: A guide to methods and applications* (Academic Press 1990), which is incorporated herein by reference; see, also, Sambrook et al., supra, 1989).

The present invention also provides a nucleic acid that encodes the consensus sequence active fragment IVRD-PFERL (SEQ ID NO:14). This nucleic acid is exemplified by human sequence ATT GTA AGA GAT CCC TTC GAA AGA CTT (SEQ ID NO:14) and mouse sequence ATT GTG AGA GAT CCC TTT GAA AGA CTG (SEQ ID NO:16).

The HNK-1 carbohydrate is associated with a number of cell adhesion molecules in the nervous tissues. The addition of the HNK-1 glycan to these various adhesion molecules can be involved in the modulation of cell-cell and cell-substratum interactions. The huHNK-1ST cDNA therefore provides a powerful molecular tool to manipulate the expression level of the HNK-1 glycan in specific cell types, allowing a dissection of the intricate and complex cell processes of cell-cell interactions during development.

Neurite outgrowth of motor neurons over cryosections of ventral roots can be inhibited by preincubation with anti-HNK-1 antibody. Moreover, a substratum containing laminin and HNK-1 glycolipid facilitates neurite outgrowth better than laminin containing ether glycolipids. These results strongly suggest that HNK-1 glycan promotes neurite outgrowth of motor neurons (Martini et al., (1992) Eur. J. Neurosci. 4, 628–639). In conjunction with the fact that the HNK-1 glycan is expressed in myelinating Schwann cells, it also has been suggested that the HNK-1 glycan has a role in myelination (Schachner and Martini, (1995) Trends Neurosci. 18, 183–191). In hematopoietic cells and tumor cells, HNK-1 glycan, but not sialyl Le$^x$, is a P-selectin ligand in CD24 (Aigner et al., (1997) Blood 89, 3385–3395). CD24 also was enriched in small cell lung carcinoma cells (Jackson et al., (1992) Cancer Res. 52, 5264–5270). These results suggest that HNK-1 glycan can be a tumor-associated antigen in certain cells and may be involved in tumor cell adhesion to platelets and endothelial cells.

The invention further provides methods of synthesizing an HNK-1 carbohydrate epitope on a glycoprotein or glycolipid precursor, by contacting the precursor with human HNK-1ST. Such contacting can occur in vitro or in vivo and, when performed in vitro, can be performed in a cell-free system using a substantially purified precursor or using cells, which express the precursor, in culture. The invention also provides a method of functional expression cloning, the general methods of which are well known in the art, but have not been applied to HNK-1 sulfotransferases.

The following examples are intended to illustrate but not limit the invention.

EXAMPLE I

Expression Cloning of Human HNK-1ST

This example describes the expression cloning of human HNK-1ST.

A. Preparation of Recipient Cells and Plasmids

A mutant cell line of Chinese hamster ovary cells, Lec2, was used as recipient cells. β-glucuronylation of N-acetyllactosamines is extremely efficient in Lec2 cells (Terayama et al., (1997) Proc. Natl. Acad. Sci. U.S.A. 94, 6093–6098.) because sialylation is absent in this cell line (Deutscher et al., (1984) Cell 39, 295–299.). Lec2 cells were first transfected with pHβAPr-1-neo-NCAM 140 (Dickson et al., (1987) Cell 50, 1119–1130.) and a stable cell line expressing human N-CAM, Lec2-NCAM, was selected as described before (Nakayama et al., (1995) Proc. Natl. Acad. Sci., U.S.A. 92, 7031–7035).

For cloning of GlcAT-P, the cDNA was synthesized from poly-A$^+$RNA of rat brain (Clontech) using a reverse transcriptase-polymerase chain reaction ("RT-PCR") kit (Stratagene). Using the cDNA molecules synthesized as templates, PCR was performed to amplify the GlcAT-P sequence as previously described (Nakayama et al., (1996) J. Biol. Chem. 271, 3684–3691). The 5'- and 3'-primers correspond to nucleotides −32 to −10 and nucleotides 1047–1027, respectively of the reported rat GlcAT-P sequence (Terayama et al., (1997) Proc. Natl. Acad. Sci. U.S.A. 94, 6093–6098). The 5'- and 3'-primers also contain HindIII and XhoI sites, respectively. The PCR product was digested with HindIII and XhoI, then cloned into pcDNA3, resulting in pcDNA3-GlcAT-P.

B. Isolation of a Human HNK-1ST cDNA Clone

Lec2-NCAM cells were negative for the HNK-1 antigen after pcDNA3-GlcAT-P was transiently expressed. Thus, Lec2-NCAM cells were co-transfected with 18 μg of a human fetal brain cDNA library in pcDNAI (Nakayama et al., (1995) Proc. Natl. Acad. Sci., U.S.A. 92, 7031–7035), 6 μg of pcDNA3-GlcAT-P and 6 μg of pPSVE1-PyE harboring the polyoma large T cDNA (Bierhuizen and Fukuda, (1992) Proc. Natl. Acad. Sci., U.S.A. 89, 9326–9330), using LIPO-FECTAMINE (Gibco-BRL; Gaithersburg MD; see also Nakayama et al., (1995) Proc. Natl. Acad. Sci., U.S.A. 92, 7031–7035.). After 62 hr, the transfected cells were dissociated into monodispersed cells using the enzyme-free cell dissociation solution (Hank's based; Cell and Molecular Technologies; Lavellette N.J.), followed by fluorescence activated cell sorting of the HNK-1 positive cells using anti-HNK-1 monoclonal antibody (Becton Dickinson).

Plasmid DNA from the sorted cells was isolated by the Hirt procedure (Hirt, (1967) J. Mol. Biol. 26, 365–369) and amplified in the host bacteria, *Escherichia coli* MC1061/P3, in the presence of ampicillin and tetracycline. The pcDNAI vector contains the supF suppressor tRNA, so that MC1061/P3 cells containing pcDNAI are resistant to both ampicillin and tetracycline. In contrast, MC1061/P3 cells harboring pcDNA3-GlcAT-P or pPSVE1-PyE are resistant to ampicillin but not to tetracycline. Because of this difference, only plasmids derived from pcDNAI were rescued and amplified by this procedure (Nakayama et al., (1995) Proc. Natl. Acad. Sci., U.S.A. 92, 7031–7035), allowing the isolation of plasmids responsible for the HNK-1 glycan expression.

Bacteria harboring plasmids were isolated from the Lec2-NCAM cells, which were sorted once, and were divided into 20 plates. Plasmid DNA was prepared from each plate and separately transfected into Lec2-NCAM cells together with pcDNA3-GlcAT-P. The transfectants were screened by immunofluorescence microscopy using anti-HNK-1 antibody to identify a plasmid pool that directed the expression of the HNK-1 glycan. Plasmid DNA, recovered from anti-HNK-1 antibody positive Lec2-NCAM cells, was immediately subjected to sibling selection with sequentially smaller, active pools, identifying a single clone containing the plasmid, pcDNAI-HNK-1ST, that directed the expression of the HNK-1 glycan. Weak staining was observed when only huHNK-1ST was present, probably due to endogenous expression of a small amount of GLcAT-P. No staining was observed when huHNK-1ST cDNA was not expressed.

Nucleotide sequences were determined in both strands by an automated sequencer (Applied Biosystems 377XL; Mountain View Calif.). The nucleotide sequence of the cDNA insert encoding huHNK-1ST is shown in FIG. 1 (SEQ ID NO:1). The cDNA contains an open reading frame (ORF) encoding a protein having 356 amino acid residues (SEQ ID NO:3, which is shown at positions 1 to 1068 enclosed by brackets in FIG. 1 and stop codon 1067 to 1071 in FIG. 1) 42,206 Da; FIG. 1). A hydropathy plot predicts that this protein has a type II membrane topology, and the transmembrane domain (residues 5–22) is flanked by basic amino acids. This topology has been found in almost all mammalian glycosyltransferases so far cloned (Schachter, (1994) in Molecular Glycobiology, eds. Fukuda and Hindsgaul, (Oxford Univ. Press, Oxford), pages 88–162).

No significant similarity between the cloned huHNK-1ST and sequences for other proteins deposited in GenBank was revealed. However, the amino acid sequence of residues 187–195 (see the doubly underlined sequence in FIG. 1 and in the consensus sequence discussed above) shares homology with sequences found in other Golgi-associated sulfotransferases such as chick chondroitin sulfate 6-O-sulfotransferase, human galactosylceramide sulfotransferase, hamster heparan sulfate 2-O-sulfotransferase and human heparan sulfate 3-O-sulfotransferase (Fukuta et al., (1995) J. Biol. Chem. 270, 18575–18580; Honke et al., (1997) J. Biol. Chem. 272, 4864–4868; Kobayashi et al., (1997) J. Biol. Chem. 272, 13980–13985; Shworak et al., (1997) J. Biol. Chem. 272, 28008–28019). In particular, the "RDP" sequence (residue 189–191) is completely conserved and hydrophobic amino acids are shared among these amino acid sequences. Recently, the amino acid sequence of a rat HNK-1ST was reported (Bakker et al., (1997) J. Biol. Chem. 272, 29942–29946). The rat HNK-1ST amino acid sequence has the identical sequence as the human HNK-1ST in residues 187–195 (see also FIG. 4).

C. Construction of Vectors Harboring Short 5'- and 3'-Untranslated Sequences

In order to determine if translation begins at the presumed initiator methionine, a truncated cDNA starting from 9 bp upstream of the initiation codon was constructed in pcDNA3, yielding pcDNA3-HNK-1ST (ORF). To shorten the long 3'-untranslated sequence of pcDNAI-HNK-1ST, the huHNK-1ST cDNA was digested utilizing an internal EcoRI site, which is located 15 nucleotides downstream of the stop codon, and cloned into pcDNA3, resulting in pcDNA3-HNK-1ST (short). A truncated cDNA containing only 9 and 6 nucleotides of 5'- and 3'-untranslated sequences, respectively, in addition to the coding sequence was prepared by PCR. The 5'- and 3'-primers for PCR were 5'-GTC AAGCTTTGTGACAAACATGCACCACCAGTGG- CT-3' (SEQ ID NO:10) and 5'-GCGCTCGAGTATGCA-TTAGTTTAGCAAAAAGTC-3'(SEQ ID NO:11), respectively. HindIII and XhoI sites are underlined while huHNK-1ST coding sequences are shown in bold. After restriction enzyme digestion, the PCR product was cloned into pcDNA3, yielding pcDNA3-HNK-1ST (ORF). This plasmid directed the expression of the HNK-1 carbohydrate, confirming that nucleotides 1–1068 encode the coding region of huHNK-1ST (FIG. 1).

Further analysis of the human HNK-1ST amino acid sequence revealed the presence of three potential N-glycosylation sites (see FIG. 1, asterisks; SEQ ID NO:2). A consensus sequence for polyadenylation signal is present at nucleotides 2432–2437 followed by a poly-A tail (SEQ ID NO;1). Judging from the size of the mRNA (see below), the entire cDNA (2877 bp) nearly covers the full length transcript.

EXAMPLE II

Expression of Human HNK-1ST

This example demonstrates that the cloned huHNK-1ST transfers a sulfate group to C-3 of GlcA attached to N-acetyllactosamine, forming sulfo→3GlcAβ1→3Galβ1→4GlcNAcβ1→R.

A. Northern Blot Analysis of Various Human Tissues

Human multiple tissue northern blots of poly-A$^+$RNA (Clontech) were hybridized sequentially with gel purified cDNA inserts of pcDNA3-HNK-1ST (ORF) and pcDNA3-GlcAT-P, after labeling with $^{32}$P-dCTP by random oligonucleotide primers (PRIME-IT II labeling kit; Stratagene). An huHNK-1ST transcript of approximately 3 kb was prominently detected in fetal brain, moderately in lung and kidney but barely in liver. The same transcript was strongly detected in adult brain, testis, ovary and moderately in heart, skeletal muscle, pancreas, spleen, and thymus, but weakly in other tissues. Among various parts of the brain, huHNK-1ST transcript is expressed more in the frontal lobe than the other parts.

The transcript of GlcAT-P is almost exclusively expressed in both fetal and adult brains, similarly to that described for rat tissues (Terayama et al., (1997) Proc. Natl. Acad. Sci. U.S.A. 94, 6093–6098). Moreover, the GlcAT-P transcript is ubiquitously expressed in various parts of the brain and is most abundant in the corpus callosum and hippocampus. Since GlcAT-P is necessary to form the HNK-1 glycan in glycoproteins, expression of the HNK-1 carbohydrate in glycoproteins of nervous tissue may be determined by the regulation of GlcAT-P expression. In other tissues, huHNK-1ST may utilize acceptors other than those synthesized by GlcAT-P.

B. Western Blot Analysis of N-CAM Expressing the HNK-1 Carbohydrate

In order to determine if huHNK-1ST is capable of adding the HNK-1 epitope on N-CAM, Lec2-NCAM cells were transiently transfected with pcDNAI-HNK-1ST and pcDNA3-GlcAT-P; pcDNAI-HNK-1ST, alone; or pcDNA3-GlcAT-P, alone. Forty-eight hr after transfection, cell lysates were prepared from the transfected cells and incubated with a mouse anti-human-N-CAM monoclonal antibody (ERIC-1; Santa Cruz Biotechnology; see Bourne et al., (1991) J. Neurooncol. 10, 111–119), followed by protein G-Agarose (Pierce). After solubilization, the immunoprecipitates were separated by SDS polyacrylamide (5%) gel electrophoresis and transferred onto nitrocellulose membrane. The blot was then incubated with the anti-N-CAM antibody, anti-HNK-1 antibody or M6749 antibody (Obata and Tanaka, (1988) Neurosci. Res. 6, 131–142), followed by horseradish peroxidase-conjugated sheep anti-mouse immunoglobulins and visualized by ECL kit (Amersham).

Western blot analysis revealed that the HNK-1 glycan was formed on N-CAM when both huHNK-1ST and GlcAT-P were expressed, whereas the HNK-1 glycan was not expressed in the absence of either enzyme. The expression of GlcAT-P, alone, resulted in binding of the M6749 antibody, which was shown to react with both sulfated and non-sulfated forms of the HNK-1 carbohydrate (Terayama et al., (1997) Proc. Natl. Acad. Sci. U.S.A. 94, 6093–6098; Obata and Tanaka, (1988) Neurosci. Res. 6, 131–142). These results clearly establish that huHNK-1ST forms the HNK-1 carbohydrate epitope on N-CAM when a glucuronyl precursor structure is present.

C. Expression of the Protein A-huHNK-1ST Fusion Protein

The cDNA fragment encoding the stem region plus catalytic domain of huHNK-1ST was prepared by PCR using pcDNA3-HNK-1ST (short) as a template and fused with the cDNA encoding a signal peptide sequence and the IgG binding domain of *Staphylococcus aureus* protein A (Nakayama and Fukuda, (1996) J. Biol. Chem. 271, 1829–1832; Sasaki et al., (1993) J. Biol. Chem. 268, 22782–22787). The 5'-primer for PCR was 5'-TT<u>AGATCT</u>ACCAGATGTGTACAGTGCC-3'(SEQ ID NO:17), where the BglII site is underlined and the coding sequence of huHNK-1ST is shown in bold. The 3'-primer was the SP6 promoter sequence. The PCR product was digested by BglII and XhoI, then cloned into BamHI and XhoI sites of pcDNAI-A (Nakayama and Fukuda, (1996) J. Biol. Chem. 271, 1829–1832), yielding pcDNAI-A•HNK-1ST. pcDNAI-A•HNK-1ST and pcDNAI-A were separately transfected to COS-1 cells and the soluble chimeric enzyme was adsorbed to IgG-SEPHAROSE 6FF (Pharmacia; see Nakayama and Fukuda, (1996) J. Biol. Chem. 271, 1829–1832.).

D. Assay of In Vitro Activity of huHNK-1ST

Galβ1→4GlcNAcβ1→octyl, GlcAβ1→3Galβ1→4GlcNAc↑1→octyl, sulfo→3GlcAβ1→3Galβ1→4GlcNAcβ1→octyl were synthesized as previously described (Ding et al., (1996) Bioorganic. Med. Chem. 4, 683–692; Isogai et al., (1996) J. Carbohyd. Chem. 15, 1119–1137.), except that octyl 2-acetamido-2 deoxy-β-D-glucopyranoside was used as the starting material. Key 1H NMR (600 MHZ, D20) for GlcAβ1→3Galβ1→4GlcNAcβ1→octyl is included; δ4.680 (d, J=8.0 Hz, H-1 GlcA), 4.520 (sec. order, J1,2=8.1 Hz) and 4.502 (d, J=7.9 Hz) (H-1 Gal and H-1 Glc), 4.190 (d, J=3.1, H-4 Gal), 2.040 (s, NCOCH3). GlcAβ1→3Galβ1→4GlcNAcβ1→3Galβ1→4Glc→ceramide was prepared by acid hydrolysis from its sulfated form (Chou et al., (1986) J. Biol. Chem. 261, 11717–11725).

The reaction mixtures (100 µl total) contained 0.02 mM $^{35}$S-PAPS, 25 µl of IgG bead-bound enzyme suspension, 0.1 mM acceptor oligosaccharides or 0.0265 mM acceptor glycolipids in 100 mM Tris-HCl (pH 7.2), 0.1% Triton X-100, 10 mM MnCl$_2$ and 2.5 mM ATP (Chou and Jungalwala, (1993) J. Biol. Chem. 268, 330–336). After incubation for 2 hr at 37° C., the reaction products were adjusted to 0.25 M ammonium formate, pH 4.0 and applied to a C18 reverse phase column (Alltech). After washing the column with the same solution, the product was eluted with 70% methanol.

In order to prove that the cloned cDNA encodes huHNK-1ST, the soluble huHNK-1ST (see Example II.C., above) was incubated with acceptor oligosaccharides or glycolipid and $^{35}$S-PAPS. The enzyme adsorbed to IgG-SEPHAROSE from COS-1 cells transfected with pcDNAI-A (lanes 1, 3 and 5) or with pcDNAI-A•HNK-1ST (lanes 2, 4 and 6) was incubated with Galβ1→4GlcNAcβ1→octyl (lanes 1 and 2); GlcAβ1→3Galβ1→4GlcNAcβ1→octyl (lanes 3 and 4); or GlcAβ1→3Galβ1→4GlcNAcβ1→3Galβ1→4Glc→ceramide (lanes 5 and 6). The activity is expressed as pmoles of sulfate transferred from 3'-phosphoadenosine 5'-phosphosulfate (PAPS) per hour per ml of the culture medium. The results are as follows:

| Lane | activity (pmol/h/mL) |
|------|---------------------|
| 1 | 0.7 |
| 2 | 0.8 |
| 3 | 0.7 |
| 4 | 16.0 |
| 5 | 1.8 |
| 6 | 5.2 |

As shown, a substantial amount of $^{35}$S-sulfate was incorporated to GlcAβ1→3Galβ1→4GlcNAcβ1→octyl (lane 4), while no incorporation was detected using the medium from mock-transfected COS-1 cells (lane 3), or using Galβ1→4GlcNAcβ→octyl as an acceptor (lane 2). Similarly, $^{35}$S-sulfate was incorporated into the glycolipid acceptor (lane 6). Considering that the concentration of the oligosaccharide acceptors is 3.8 times higher than that of the glycolipid acceptor, huHNK-1ST added sulfate to the oligosaccharide as efficiently as it added sulfate to the glycolipid.

The reaction products shown in lanes 2 to 6 were subjected to thin layer chromatography followed by autoradiography. Thin layer chromatography was carried out on the products obtained by the enzyme derived from pcDNAI-A or pcDNAI-HNK-1ST and subjected to autoradiography. The products were separated by thin layer chromatography using silica gel. After separation in chloroform:methanol:0.25% KCl (5:4:1, v/v/v), the thin layer plate was exposed to X-ray film (Kodak BioMax) for 16 hr at room temperature. Standard oligosaccharides were then detected by spraying with 0.2% orcinol in 2 M H$_2$SO$_4$. The sulfated product migrated at the same position of a standard synthetic oligosaccharide, sulfo→3GlcAβ1→3Galβ1→4GlcNAcβ1→octyl. These results establish that the cloned huHNK-1ST transfers a sulfate group to C-3 of GlcA attached to N-acetyllactosamine, forming sulfo→3GlcAβ1→3Galβ1→4GlcNAcβ1→R.

EXAMPLE III

Effect of HNK-1Glycan on Neurite Outgrowth

This example demonstrates that cells expressing N-CAM and HNK-1 glycan promote greater neurite outgrowth than cells expressing N-CAM, but not HNK-1.

HeLa cells stably expressing the human N-CAM 140 (HeLa-NCAM) were established as previously described (Nakayama et al., (1995) Proc. Natl. Acad. Sci., U.S.A. 92, 7031–7035). HeLa-NCAM cells stably expressing glucuronic acid (HeLa-NCAM-GlcA) were established by co-transfection of HeLa-NCAM cells with pcDNA3-GlcAT-P and pSV2-hygro, using SUPERFECT (Qiagen). HeLa-NCAM cells stably expressing HNK-1 were established by transfection of HeLa-NCAM-GlcA with pcDNA3.1/zeo-HNK-1ST.

The variously transfected HeLa cells were cultured as monolayers by seeding 100,000 cells onto 13 mm round glass coverslips that had been coated with poly-L-lysine (13 µg/ml). The cells reached confluency after approximately 2 days. Single cell suspensions of post-natal day 5 rat cerebellar neurons were prepared as previously described (Groves et al., (1993) Dev. Biol. 159, 87–104). 20,000 neurons were plated onto each monolayer and cultured for 24 hr, then fixed and stained for GAP-43 immunoreactivity (Doherty et al., (1992) Nature 356, 791–793).

GAP-43-labeled neurons were detected by fluorescence microscopy using a video camera and analyzed using the METAMORPH image analysis software as previously described (Nakayama et al., (1995) Proc. Natl. Acad. Sci., U.S.A. 92, 7031–7035). Cultures were scanned in a systematic manner and the length of the longest GAP-43-positive neurite measured. Only neurons with at least one neurite exceeding 30 μm were included in the analysis. At least 100 such neurons, from two separate coverslips, were measured for each condition and the mean neurite length was compared using a one-tailed Student t-test.

As shown in FIG. 5, HeLa-NCAM cells expressing HNK-1 glycan supported the neurite outgrowth much better than those expressing glucuronic acid containing precursors or N-CAM alone. The mean value of neurite lengths extended on the HeLa-NCAM cells expressing HNK-1 was 154 μm±49 μm (average deviation), while those grown on control HeLa-NCAM cells and HeLa-NCAM-GlcA cells was 125 μm±45 μm and 129 μm±45 μm, respectively ($p<0.01$). These results demonstrate that expression of sulfated HNK-1 glycan facilitates neurite outgrowth.

Although the invention has been described with reference to the examples provided above, it should be understood that various modifications can be made without departing from the spirit of the invention.

We claim:

1. A nucleic acid isolated from human and having SEQ ID NO:1.
2. An isolated nucleic acid that encodes human amino acid SEQ ID NO:2.
3. A nucleic acid isolated from human and having SEQ ID NO:3.
4. A nucleic acid isolated from mouse and having SEQ ID NO:12.
5. An isolated nucleic acid that encodes mouse amino acid SEQ ID NO:13.
6. An isolated nucleic acid consisting of the sequence ATT GTG AGA GAT CCC TTT GAA AGA CTG (SEQ ID NO:16).

* * * * *

SEQUENCE LISTING

```
<160> NUMBER OF SEQ ID NOS: 17

<210> SEQ ID NO 1
<211> LENGTH: 2877
<212> TYPE: DNA
<213> ORGANISM: Homo sapiens
<220> FEATURE:
<221> NAME/KEY: CDS
<222> LOCATION: (387)..(1457)

<400> SEQUENCE: 1
cggccggata ggcgcgaggg ggccgcgtga ggcggtgccg gcgttctggc ccccaaagcc      60
ggtctagcgc gccgggcgtc ttccttactt ccgctgccgc cgccgccaca tcccgggacc     120
cgacgggccg cggcgcggag gcctcggggc aaggtggggc gggcctcccg agctcccagg     180
accccgcgcg cttcgcccac aggcccggcg aagcccgacc cgcgcggcgc ccccaggggcc    240 agggggaggag cctaaggacc cggacgagcg ccgctccagt aggtgacaag aggaaacaag    300
aacctcagtt caggggaaac acagcaagga aatgtgagcc ccaggctgca gaaggaagag    360
tcagtgaatg gctgcggtgt gacaac atg cac cac cag tgg ctt ctg ctg gcc    413
                              Met His His Gln Trp Leu Leu Leu Ala
                                1               5 gca tgc ttt tgg gtg att ttc atg ttc atg gtg gct agc aag ttc atc     461
Ala Cys Phe Trp Val Ile Phe Met Phe Met Val Ala Ser Lys Phe Ile
 10              15                  20                  25 acg ttg acc ttt aaa gac cca gat gtg tac agt gcc aaa cag gag ttt     509
Thr Leu Thr Phe Lys Asp Pro Asp Val Tyr Ser Ala Lys Gln Glu Phe
                 30                  35                  40 ctg ttc ctg aca acc atg ccg gaa gtg agg aag ttg cca gaa gag aag     557
Leu Phe Leu Thr Thr Met Pro Glu Val Arg Lys Leu Pro Glu Glu Lys
             45                  50                  55 cac att cct gag gaa ctg aag cca act ggg aag gag ctt cca gac agc     605
His Ile Pro Glu Glu Leu Lys Pro Thr Gly Lys Glu Leu Pro Asp Ser
         60                  65                  70 cag ctc gtt cag ccc ctg gtc tac atg gag cgc ctg gaa ctc atc aga     653
Gln Leu Val Gln Pro Leu Val Tyr Met Glu Arg Leu Glu Leu Ile Arg
     75                  80                  85 aac gtc tgc agg gat gat gcc ctg aag aat ctc tcg cac act cct gtc     701
Asn Val Cys Arg Asp Asp Ala Leu Lys Asn Leu Ser His Thr Pro Val
 90                  95                 100                 105 tcc aag ttt gtc ctg gac cga ata ttt gtc tgt gac aag cac aag att     749
Ser Lys Phe Val Leu Asp Arg Ile Phe Val Cys Asp Lys His Lys Ile
                110                 115                 120 ctt ttc tgc cag act ccc aaa gtg ggc aac acc cag tgg aag aaa gtg     797
```

```
Leu Phe Cys Gln Thr Pro Lys Val Gly Asn Thr Gln Trp Lys Lys Val
            125                 130                 135 ctg att gtt cta aat gga gca ttt tct tcc att gag gag atc ccc gaa      845
Leu Ile Val Leu Asn Gly Ala Phe Ser Ser Ile Glu Glu Ile Pro Glu
            140                 145                 150 aac gtg gtg cac gac cac gag aag aac ggc ctt cct cgg ctc tct tcc      893
Asn Val Val His Asp His Glu Lys Asn Gly Leu Pro Arg Leu Ser Ser
            155                 160                 165 ttc agt gat gca gaa att cag aag cga ttg aaa aca tac ttc aag ttt      941
Phe Ser Asp Ala Glu Ile Gln Lys Arg Leu Lys Thr Tyr Phe Lys Phe
170                 175                 180                 185 ttt att gta aga gat ccc ttc gaa aga ctt att tct gca ttt aag gat      989
Phe Ile Val Arg Asp Pro Phe Glu Arg Leu Ile Ser Ala Phe Lys Asp
                190                 195                 200 aaa ttt gtt cac aat ccc cgg ttt gag cct tgg tac agg cat gag att     1037
Lys Phe Val His Asn Pro Arg Phe Glu Pro Trp Tyr Arg His Glu Ile
            205                 210                 215 gct cct ggc atc atc aga aaa tac agg agg aac cgg aca gag acg cgg     1085
Ala Pro Gly Ile Ile Arg Lys Tyr Arg Arg Asn Arg Thr Glu Thr Arg
            220                 225                 230 ggg atc cag ttt gaa gat ttc gtg cgc tac ctc ggc gat ccg aac cac     1133
Gly Ile Gln Phe Glu Asp Phe Val Arg Tyr Leu Gly Asp Pro Asn His
235                 240                 245 aga tgg cta gac ctt cag ttt ggg gac cac atc att cac tgg gtg acg     1181
Arg Trp Leu Asp Leu Gln Phe Gly Asp His Ile Ile His Trp Val Thr
250                 255                 260                 265 tat gta gag ctc tgt gct ccc tgt gag ata atg tac agt gtg att gga     1229
Tyr Val Glu Leu Cys Ala Pro Cys Glu Ile Met Tyr Ser Val Ile Gly
                270                 275                 280 cac cac gag acc ctg gag gac gat gcc cca tac atc tta aaa gag gct     1277
His His Glu Thr Leu Glu Asp Asp Ala Pro Tyr Ile Leu Lys Glu Ala
            285                 290                 295 ggc att gac cac ctg gtg tca tac ccg act atc cct ccg ggc att acc     1325
Gly Ile Asp His Leu Val Ser Tyr Pro Thr Ile Pro Pro Gly Ile Thr
            300                 305                 310 gtg tat aac aga acc aag gtg gag cac tat ttc ctg ggc atc agc aaa     1373
Val Tyr Asn Arg Thr Lys Val Glu His Tyr Phe Leu Gly Ile Ser Lys
            315                 320                 325 cga gac atc cga cgc ctg tat gcc cgt ttc gaa ggg gac ttt aag ctc     1421
Arg Asp Ile Arg Arg Leu Tyr Ala Arg Phe Glu Gly Asp Phe Lys Leu
330                 335                 340                 345 ttt ggg tac cag aaa cca gac ttt ttg cta aac taa tgcataagac          1467
Phe Gly Tyr Gln Lys Pro Asp Phe Leu Leu Asn
                350                 355 ctatgaattc aaatatcttt attagacctg gggctaacca ggtgaagatc tgagcccaga  1527
aatgacccct cctccaccac accctctcct tgaggatgcc cggggtctcc cacaggcctg  1587
tgagttgcct cggcatatga cgcagaaccc caactgttac aacttagttt ggatgtaaga  1647
tgctctgagg accctgccca caccctgcg tgcattagga tgtcgctggc ctttgctcac   1707
ctcagagggg agaaaggct aaagatttgc agtttgacag cccagcaggg aggaagcatc   1767
acacagcgtt aggagccgtt ccttcaggt gttaaggaag gggatgcccc tgaggttctc   1827
ctggctagtc ggggtggctt cacccatcac tggtgggttg caggaacagc acccaggact  1887
ctgaggaggg acagagaagc aaggggggctg ctgaaatcgc agagacttt gcagcatcag  1947 atctgaggag taaaacggca cctctggcct tcatcttggt gctgcgacaa ttgtggaggc  2007
aaagcattct ttctgtgact attttgttcc tgtagacagt cagcgatggc cagagggtgg  2067
```

-continued

```
tgtggtgtcc agggtccat ctttccagaa tccatgcctg tgtaatgctg gtccatgctt    2127
ctgaacctgt gtctgccaag cgcctatttc attcagcaca agacatacga ttttagaagg    2187
tgagggagg ggaggctttt tctacctgag aagggagtg tctttgaggg ccttaaaagg      2247
accatggccc aggaatgggg gcgctggttg ggcttggagc tcaggctgct gtggatcccg    2307
gcgcatcagt tctgacttgc cttacctggg tggacagcag tgaatctcca cctgtcttct    2367
ccagggagct cccatgttgg ggctgaagac gagcaggggc aacctgccag catcacagaa    2427
ttcagtgtag tttatacatt tcgattcctt tcatctcagc aaaatgggca ctgccagagc    2487
catttctgat cacaccacca tcctggacca tgtgactgga aggtgggtaa ccaagttcac    2547
cagcaataaa acccagcgcc caggtagcct ccagcagtgc ggcttcctgg caacaaggta    2607
ggccctggtg cagggcaagc cgcagcgacc atttcagata ccgtccacag ccaggaccgc    2667
tgagaactgg gacagtttcc tgggatgagt gccagcctga gcctgcatgg tgccgccgag    2727
cccggggtgg aggagggagc caggcttcgc ttcaaggcgg cctctaccct ttctcagaat    2787
ggtttcctga ttgtgtcaat gtgaaagtta aataaaattt atgtgccaaa aaaaaaaaa     2847
aaaaaaaaaa aaaaaaaaaa aaaaaaaaa                                       2877
```

<210> SEQ ID NO 2
<211> LENGTH: 356
<212> TYPE: PRT
<213> ORGANISM: Homo sapiens

<400> SEQUENCE: 2

```
Met His His Gln Trp Leu Leu Leu Ala Ala Cys Phe Trp Val Ile Phe
 1               5                  10                  15

Met Phe Met Val Ala Ser Lys Phe Ile Thr Leu Thr Phe Lys Asp Pro
             20                  25                  30

Asp Val Tyr Ser Ala Lys Gln Glu Phe Leu Phe Leu Thr Thr Met Pro
         35                  40                  45

Glu Val Arg Lys Leu Pro Glu Glu Lys His Ile Pro Glu Glu Leu Lys
     50                  55                  60

Pro Thr Gly Lys Glu Leu Pro Asp Ser Gln Leu Val Gln Pro Leu Val
 65                  70                  75                  80

Tyr Met Glu Arg Leu Glu Leu Ile Arg Asn Val Cys Arg Asp Asp Ala
                 85                  90                  95

Leu Lys Asn Leu Ser His Thr Pro Val Ser Lys Phe Val Leu Asp Arg
            100                 105                 110

Ile Phe Val Cys Asp Lys His Lys Ile Leu Phe Cys Gln Thr Pro Lys
        115                 120                 125

Val Gly Asn Thr Gln Trp Lys Lys Val Leu Ile Val Leu Asn Gly Ala
    130                 135                 140

Phe Ser Ser Ile Glu Glu Ile Pro Glu Asn Val Val His Asp His Glu
145                 150                 155                 160

Lys Asn Gly Leu Pro Arg Leu Ser Ser Phe Ser Asp Ala Glu Ile Gln
                165                 170                 175

Lys Arg Leu Lys Thr Tyr Phe Lys Phe Ile Val Arg Asp Pro Phe
            180                 185                 190

Glu Arg Leu Ile Ser Ala Phe Lys Asp Lys Phe Val His Asn Pro Arg
        195                 200                 205

Phe Glu Pro Trp Tyr Arg His Glu Ile Ala Pro Gly Ile Ile Arg Lys
    210                 215                 220

Tyr Arg Arg Asn Arg Thr Glu Thr Arg Gly Ile Gln Phe Glu Asp Phe
```

```
225                 230                 235                 240
Val Arg Tyr Leu Gly Asp Pro Asn His Arg Trp Leu Asp Leu Gln Phe
                245                 250                 255
Gly Asp His Ile Ile His Trp Val Thr Tyr Val Glu Leu Cys Ala Pro
            260                 265                 270
Cys Glu Ile Met Tyr Ser Val Ile Gly His His Glu Thr Leu Glu Asp
        275                 280                 285
Asp Ala Pro Tyr Ile Leu Lys Glu Ala Gly Ile Asp His Leu Val Ser
    290                 295                 300
Tyr Pro Thr Ile Pro Pro Gly Ile Thr Val Tyr Asn Arg Thr Lys Val
305                 310                 315                 320
Glu His Tyr Phe Leu Gly Ile Ser Lys Arg Asp Ile Arg Arg Leu Tyr
                325                 330                 335
Ala Arg Phe Glu Gly Asp Phe Lys Leu Phe Gly Tyr Gln Lys Pro Asp
            340                 345                 350
Phe Leu Leu Asn
        355

<210> SEQ ID NO 3
<211> LENGTH: 1068
<212> TYPE: DNA
<213> ORGANISM: Homo sapiens

<400> SEQUENCE: 3
atgcaccacc agtggcttct gctggccgca tgcttttggg tgattttcat gttcatggtg      60
gctagcaagt tcatcacgtt gacctttaaa gacccagatg tgtacagtgc caaacaggag     120
tttctgttcc tgacaaccat gccggaagtg aggaagttgc cagaagagaa gcacattcct     180
gaggaactga agccaactgg gaaggagctt ccagacagcc agctcgttca gcccctggtc     240
tacatggagc gcctggaact catcagaaac gtctgcaggg atgatgccct gaagaatctc     300
tcgcacactc ctgtctccaa gtttgtcctg gaccgaatat ttgtctgtga caagcacaag     360
attcttttct gccagactcc caagtgggc aacacccagt ggaagaaagt gctgattgtt     420
ctaaatggag catttttcttc cattgaggag atccccgaaa acgtggtgca cgaccacgag     480
aagaacggcc ttcctcggct ctcttccttc agtgatgcag aaattcagaa gcgattgaaa     540
acatacttca gttttttat tgtaagagat cccttcgaaa gacttatttc tgcatttaag     600
gataaatttg ttcacaatcc ccggtttgag ccttggtaca gcatgagat tgctcctggc     660 atcatcagaa aatacaggag gaaccggaca gagacgcggg ggatccagtt tgaagatttc     720
gtgcgctacc tcggcgatcc gaaccacaga tggctagacc ttcagtttgg ggaccacatc     780
attcactggg tgacgtatgt agagctctgt gctccctgtg agataatgta cagtgtgatt     840
ggacaccacg agaccctgga ggacgatgcc ccatacatct aaaagaggc tggcattgac     900 cacctggtgt catacccgac tatccctccg ggcattaccg tgtataacag aaccaaggtg     960
gagcactatt tcctgggcat cagcaaacga gacatccgac gcctgtatgc ccgtttcgaa    1020
ggggacttta agctcttttgg gtaccagaaa ccagacttttt gctaaac                 1068

<210> SEQ ID NO 4
<211> LENGTH: 356
<212> TYPE: PRT
<213> ORGANISM: Rattus norvegicus

<400> SEQUENCE: 4
```

-continued

```
Met His His Gln Trp Leu Leu Leu Ala Ala Cys Phe Trp Val Ile Phe
 1               5                  10                  15

Met Phe Met Val Ala Ser Lys Phe Ile Thr Leu Thr Phe Lys Asp Pro
                20                  25                  30

Asp Gly Tyr Ser Ala Lys Gln Glu Phe Val Phe Leu Thr Ala Met Pro
            35                  40                  45

Glu Ala Glu Lys Leu Arg Gly Glu Lys His Phe Ser Glu Val Met Lys
        50                  55                  60

Pro Thr Gly Lys Met Leu Ser Glu Ser His Pro Asp Gln Pro Pro Val
 65                  70                  75                  80

Tyr Leu Glu Arg Leu Glu Leu Ile Arg Asn Ala Cys Lys Glu Glu Ala
                85                  90                  95

Leu Arg Asn Leu Ser His Thr Glu Val Ser Lys Phe Val Leu Asp Arg
                100                 105                 110

Ile Phe Val Cys Asp Lys His Lys Ile Leu Phe Cys Gln Thr Pro Lys
            115                 120                 125

Val Gly Asn Thr Gln Trp Lys Lys Val Leu Ile Val Leu Asn Gly Ala
130                 135                 140

Phe Ser Ser Ile Glu Glu Ile Pro Glu Asn Val Val His Asp His Glu
145                 150                 155                 160

Lys Asn Gly Leu Pro Arg Leu Ser Ser Phe Ser Lys Ile Gly Ile Gln
                165                 170                 175

Lys Arg Leu Lys Thr Tyr Phe Lys Phe Phe Ile Val Arg Asp Pro Phe
                180                 185                 190

Glu Arg Leu Ile Ser Ala Phe Lys Asp Lys Phe Val His Asn Pro Arg
                195                 200                 205

Phe Glu Pro Trp Tyr Arg His Glu Ile Ala Pro Gly Ile Ile Arg Lys
                210                 215                 220

Tyr Arg Lys Asn Arg Thr Glu Thr Arg Gly Ile Gln Phe Glu Asp Phe
225                 230                 235                 240

Val Arg Tyr Leu Gly Asp Pro Asn Arg Arg Trp Leu Asp Leu Gln Phe
                245                 250                 255

Gly Asp His Ile Ile His Trp Val Thr Tyr Val Lys Leu Cys Ala Pro
                260                 265                 270

Cys Glu Ile Lys Tyr Ser Val Ile Gly His His Glu Thr Leu Glu Ala
                275                 280                 285

Asp Ala Pro Tyr Ile Leu Lys Glu Ala Gly Ile Asp His Leu Val Ser
                290                 295                 300

Tyr Pro Thr Ile Pro Pro Gly Ile Thr Met Tyr Asn Arg Thr Lys Val
305                 310                 315                 320

Glu Gln Tyr Phe Leu Gly Ile Ser Lys Arg Asp Ile Arg Arg Leu Tyr
                325                 330                 335

Ala Arg Phe Glu Gly Asp Phe Lys Leu Phe Gly Tyr Gln Lys Pro Asp
                340                 345                 350

Phe Leu Leu Asn
        355

<210> SEQ ID NO 5
<211> LENGTH: 9
<212> TYPE: PRT
<213> ORGANISM: Hamster sp.

<400> SEQUENCE: 5

Val Ile Arg Asp Pro Ile Glu Arg Leu
 1               5
```

<210> SEQ ID NO 6
<211> LENGTH: 9
<212> TYPE: PRT
<213> ORGANISM: Gallus gallus

<400> SEQUENCE: 6

Leu Val Arg Asp Pro Arg Ala Val Leu
 1               5

<210> SEQ ID NO 7
<211> LENGTH: 9
<212> TYPE: PRT
<213> ORGANISM: Homo sapiens

<400> SEQUENCE: 7

Val Leu Arg Asp Pro Ala Arg Leu Phe
 1               5

<210> SEQ ID NO 8
<211> LENGTH: 9
<212> TYPE: PRT
<213> ORGANISM: Homo sapiens

<400> SEQUENCE: 8

Ile Leu Arg Asp Pro Ser Glu Arg Val
 1               5

<210> SEQ ID NO 9
<211> LENGTH: 9
<212> TYPE: PRT
<213> ORGANISM: Homo sapiens

<400> SEQUENCE: 9

Leu Ile Arg Asp Pro Phe Pro Glu Ile
 1               5

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 10
gtcaagcttt gtgacaaaca tgcaccacca gtggct                                 36

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 11
gcgctcgagt atgcattagt ttagcaaaaa gtc                                    33

<210> SEQ ID NO 12
<211> LENGTH: 1071
<212> TYPE: DNA
<213> ORGANISM: Mus musculus

<400> SEQUENCE: 12
atgcaccatc agtggctcct gctggctgca tgcttttggg tgattttcat gttcatggtg       60

-continued

| | |
|---|---|
| gccagcaagt tcatcacgtt gacctttaag gatccggatg ggtatagtgc caaacaggag | 120 |
| tttgtgttcc tgacgaccat gccggaagca gagaagctaa gaggagagaa gcattttcct | 180 |
| gaagtcccga agccaactgg gaagatgctt tcggacagcc gtcctgatca gcccccggtt | 240 |
| tatctggagc ggctggagct catcagaaac acctgcaagg aggaggctct gcggaacctc | 300 |
| tcacacaccg aggtctcgaa gttcgtcctg gatcgaatat ttgtctgtga caagcacaag | 360 |
| attctttct gtcagactcc caaggtgggc aacacccagt ggaagaaagt gctgatcgtc | 420 |
| ctaaatggag cattttcttc cattgaagag attcctgaaa atgtagtcca tgaccatgag | 480 |
| aaaaatggcc ttccacgcct ctcttccttc agcaaaatag gaattcagaa gcgattgaaa | 540 |
| acatacttca gtttttat tgtgagagat ccctttgaaa gactgatttc tgcctttaag | 600 |
| gataagtttg ttcacaatcc tcgattcgag ccttggtaca ggcatgagat agccccaggc | 660 |
| attattagaa agtaccggaa gaaccggaca gagacccggg ggatccagtt tgaagatttt | 720 |
| gtgcgctacc tgggtgatcc aaaccgcagg tggttagacc ttcagtttgg ggaccatatc | 780 |
| atccactggg tgacctacgt tgaactctgt gcgccctgtg agatcaagta cagtgtggtc | 840 |
| ggacaccatg agaccctgga ggcagatgcc ccgtacatcc tgaaagaagc tggcatagac | 900 |
| catctggtgt cataccccac catccctccg ggcatcacca tgtacaacag aaccaaggta | 960 |
| gagcagtatt tcctgggcat cagcaaacga gacatctggc atctctatgc acatttygaa | 1020 |
| ggagacttta agctctttgg gtatcagaaa ccagatttct tgctaaatta a | 1071 |

<210> SEQ ID NO 13
<211> LENGTH: 356
<212> TYPE: PRT
<213> ORGANISM: Mus musculus

<400> SEQUENCE: 13

Met His His Gln Trp Leu Leu Leu Ala Ala Cys Phe Trp Val Ile Phe
1               5                   10                  15

Met Phe Met Val Ala Ser Lys Phe Ile Thr Leu Thr Phe Lys Asp Pro
                20                  25                  30

Asp Gly Tyr Ser Ala Lys Gln Glu Phe Val Phe Leu Thr Thr Met Pro
            35                  40                  45

Glu Ala Glu Lys Leu Arg Gly Glu Lys His Phe Pro Glu Val Pro Lys
        50                  55                  60

Pro Thr Gly Lys Met Leu Ser Asp Ser Arg Pro Asp Gln Pro Pro Val
65                  70                  75                  80

Tyr Leu Glu Arg Leu Glu Leu Ile Arg Asn Thr Cys Lys Glu Glu Ala
                85                  90                  95

Leu Arg Asn Leu Ser His Thr Glu Val Ser Lys Phe Val Leu Asp Arg
            100                 105                 110

Ile Phe Val Cys Asp Lys His Lys Ile Leu Phe Cys Gln Thr Pro Lys
        115                 120                 125

Val Gly Asn Thr Gln Trp Lys Lys Val Leu Ile Val Leu Asn Gly Ala
    130                 135                 140

Phe Ser Ser Ile Glu Glu Ile Pro Glu Asn Val Val His Asp His Glu
145                 150                 155                 160

Lys Asn Gly Leu Pro Arg Leu Ser Ser Phe Ser Lys Ile Gly Ile Gln
                165                 170                 175

Lys Arg Leu Lys Thr Tyr Phe Ser Phe Phe Ile Val Arg Asp Pro Phe
            180                 185                 190

Glu Arg Leu Ile Ser Ala Phe Lys Asp Lys Phe Val His Asn Pro Arg

```
                195                 200                 205
Phe Glu Pro Trp Tyr Arg His Glu Ile Ala Pro Gly Ile Ile Arg Lys
    210                 215                 220
Tyr Arg Lys Asn Arg Thr Glu Thr Arg Gly Ile Gln Phe Glu Asp Phe
225                 230                 235                 240
Val Arg Tyr Leu Gly Asp Pro Asn Arg Arg Trp Leu Asp Leu Gln Phe
                245                 250                 255
Gly Asp His Ile Ile His Trp Val Thr Tyr Val Glu Leu Cys Ala Pro
                260                 265                 270
Cys Glu Ile Lys Tyr Ser Val Val Gly His His Glu Thr Leu Glu Ala
                275                 280                 285
Asp Ala Pro Tyr Ile Leu Lys Glu Ala Gly Ile Asp His Leu Val Ser
                290                 295                 300
Tyr Pro Thr Ile Pro Pro Gly Ile Thr Met Tyr Asn Arg Thr Lys Val
305                 310                 315                 320
Glu Gln Tyr Phe Leu Gly Ile Ser Lys Arg Asp Ile Trp His Leu Tyr
                325                 330                 335
Ala His Phe Glu Gly Asp Phe Lys Leu Phe Gly Tyr Gln Lys Pro Asp
                340                 345                 350
Phe Leu Leu Asn
        355

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Consensus
      Sequence

<400> SEQUENCE: 14

Ile Val Arg Asp Pro Phe Glu Arg Leu
  1               5

<210> SEQ ID NO 15
<211> LENGTH: 27
<212> TYPE: DNA
<213> ORGANISM: Homo sapiens

<400> SEQUENCE: 15
attgtaagag atcccttcga aagactt                                         27

<210> SEQ ID NO 16
<211> LENGTH: 27
<212> TYPE: DNA
<213> ORGANISM: Mus musculus

<400> SEQUENCE: 16
attgtgagag atccctttga aagactg                                         27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 17
ttagatctac cagatgtgta cagtgcc                                         27
```